(12) United States Patent
Roder

(10) Patent No.: US 8,003,631 B2
(45) Date of Patent: Aug. 23, 2011

US008003631B2

(54) COMPOSITION AND METHOD FOR THE TREATMENT OF TAUOPATHIES

(75) Inventor: Hanno Roder, Jacksonville, FL (US)

(73) Assignee: Tautatis, Inc., Cambridge, MA (US)

( * ) Notice: Subject to any disclaimer, the term of this patent is extended or adjusted under 35 U.S.C. 154(b) by 1277 days.

(21) Appl. No.: 11/597,771

(22) PCT Filed: May 26, 2005

(86) PCT No.: PCT/US2005/018640
§ 371 (c)(1),
(2), (4) Date: Nov. 27, 2006

(87) PCT Pub. No.: WO2005/117550
PCT Pub. Date: Dec. 15, 2005

(65) Prior Publication Data
US 2007/0232584 A1    Oct. 4, 2007

(30) Foreign Application Priority Data
May 26, 2004    (DE) .......................... 10 2004 025 726

(51) Int. Cl.
*A61K 31/33*    (2006.01)
*A61K 31/41*    (2006.01)

(52) U.S. Cl. ........ 514/183; 514/359; 514/579; 514/461; 514/211.01; 540/1

(58) Field of Classification Search .................. 514/219, 514/556, 183, 211.01, 359, 461, 579; 540/556, 540/1
See application file for complete search history.

(56) References Cited

U.S. PATENT DOCUMENTS

| | | |
|---|---|---|
| 5,079,248 A | 1/1992 | Cross et al. |
| 6,451,786 B1 | 9/2002 | Hudkins et al. |
| 6,541,468 B1 | 4/2003 | Roder et al. |
| 6,677,450 B2 | 1/2004 | Saulnier et al. |
| 2002/0107237 A1 | 8/2002 | Saulnier et al. |
| 2004/0220202 A1 | 11/2004 | Jaquith et al. |
| 2005/0171182 A1 | 8/2005 | Briesewitz |
| 2006/0128780 A1 | 6/2006 | Hudkins et al. |
| 2008/0255087 A1 | 10/2008 | Roder |
| 2010/0273769 A1 | 10/2010 | Roder |

FOREIGN PATENT DOCUMENTS

| | | |
|---|---|---|
| WO | 97/05140 A1 | 2/1997 |
| WO | 98/07433 A1 | 2/1998 |
| WO | 00/01699 A1 | 1/2000 |
| WO | 2005/117550 A2 | 12/2005 |

*Primary Examiner* — Sreeni Padmanabhan
*Assistant Examiner* — Shobha Kantamneni
(74) *Attorney, Agent, or Firm* — Giulio A. DeConti, Jr.; Brian C. Trinque; Lathrop & Gage LLP

(57) ABSTRACT

The present invention refers to the use of a specific indolocarbazole compound of general formula (1) or a pharmaceutically-acceptable a salt thereof for the preparation of a pharmaceutical composition for the prevention or treatment of a neurodegenerative and/or dementing illness driven by the molecular pathology of microtubule-associate tau such as Alzheimer's disease, frontal lobe dementia, Pick's disease, Parkinson disease with dementia, corticobasal degeneration, argyrophilic grains disease, or supranuclear palsy. A method for treating or preventing such illnesses is also disclosed. Furthermore, methods for the identification of efficacious inhibitors of neurofibrillary degeneration, and methods for the determination of an appropriate dosage of an inhibitor of the PHF-type tau hyperphosphorylation for the treatment of a condition characterized by neurofibrillary pathology are described.

4 Claims, No Drawings

COMPOSITION AND METHOD FOR THE
TREATMENT OF TAUOPATHIES

FIELD OF THE INVENTION

The present invention relates to the use of specific indolocarbazole compounds for the preparation of pharmaceutical compositions for the treatment of any neurodegenerative and/or dementing illness driven by the molecular pathology of the microtubule-associated tau (hereinafter referred to as "tauopathy"). Furthermore, the present invention relates to methods for the identification of efficacious inhibitors of neurofibrillary degeneration, and methods for the determination of an appropriate dosage of an inhibitor of the paired helical filaments-type tau hyperphosphorylation in vitro for the treatment of a condition characterized by neurofibrillary pathology.

BACKGROUND OF THE INVENTION

Aberrant protein phosphorylation is now widely documented to be closely associated to the pathological aggregation of the microtubule-associated protein tau in a neurodegenerative process commonly referred to as neurofibrillary degeneration. The respective diseases, now encompassing about 22 common as well as very rare conditions, including Alzheimer's disease (AD), frontal lobe dementia (also known as frontotemporal degeneration (FTD)), corticobasal degeneration (CBD), Pick's disease (PiD), Parkinson with dementia (PDD), supranuclear palsy, argyrophilic grains disease (AGD) and a variety of lesser diseases not yet recognized by a commonly used name, all share the intracellular formation of neurofibrillary tangles (NFT) in various neuronal populations of the human brain functionally correlated with symptomatology. Irrespective of the clinical disease entity, neurofibrillary tangles are invariably composed ultrastructurally by either paired helical filaments (PHF), or less frequently by straight filaments (SF). Molecularly, paired helical filaments are exclusively composed of microtubule (MT) associated proteins tau in an abnormally hyperphosphorylated state never found in normal cell biology. In this pathological phosphorylation state, tau proteins are also unable to bind to microtubule and perform their normal physiological function of microtubule stabilization and neuron-specific organization of cytoskeleton and microtubule-dependent transport.

The dominant relevance of neurofibrillary degeneration in clinical diseases with neurofibrillary tangles, especially when collateral pathological features coexist, like in classical Alzheimer's disease, has long been conjectured but remained difficult to prove because tauopathies are found only in the human brain. The issue was unequivocally settled when certain tauopathies were found to be caused by mutations in tau, and these same mutations were able to precipitate lethal neurodegenerative phenotypes in tau-transgenic mice. Irrespective of whether paired helical filaments are produced with or without mutations in man, or with mutations in mice, the same type of pathological hyperphosphorylation of tau (PHF-tau) is invariably associated with their formation early in the process. This provides strong evidence that PHF-tau hyperphosphorylation is a common precursor pathway for neurofibrillary degeneration independent of etiology. Hence therapeutic agents interfering with this pathological phosphorylation biochemistry, e.g., by inhibition of appropriate kinases, are very likely to be effective in treating tauopathies.

Kinase inhibitors belonging to the group of glycosylated indolocarbazoles have received prominent attention in the last decade for inhibiting various kinases. The most prominent members of this class are the natural alkaloide products staurosporine and K252a. These and several other derivatives were investigated mostly for therapeutic uses in various cancer indications. WO 97/05140 describes a broad range of modified K252a derivatives, with a few compounds exemplified for therapeutic use in immunosuppression and proliferative diseases (cancer) by virtue of their PKC inhibitory activity.

So far, only one disclosure has been made about specific small molecule kinase inhibitors capable of inhibiting tau hyperphosphorylation in a cell model. Certain derivatives of synthetic analogues of K252a, which in contrast to most of the other compounds in the structural class described in the prior art, are not accessible through the natural product, showed useful potency and efficacy to prevent PHF-tau hyperphosphorylation [WO 00/01699]. These compounds, however, did not show a high degree of kinase specificity, but seemed to inhibit more than one kinase, and the synthesis could only provide for racemic compounds.

Moreover, the physicochemical properties of this series of compounds are very poor, resulting in the need to use non-GRAS (Generally Regarded As Safe under FDA guidelines) vehicles for compound application. In addition, even under specialized conditions of application, oral bioavailability for the prior art compounds usually does not exceed 10% in rats [WO 95/22331]. Possibly related to these unfortunate properties, half-lives in rats after i.v. application are unattractively short at about 1 h. Brain/plasma ratios determined in vivo as the concentration of the compound in brain over the concentration of the compound in plasma at a given time point are also poor, and deteriorate further when GRAS-vehicles are used, suggesting an unacceptable influence of vehicle on these parameters. Accordingly, chronic in vivo experiments for the inhibition of neurofibrillary pathology in authentic models, like transgenic mice carrying human pathogenic mutations of tau, cannot be conducted with such compounds.

Unfortunately, the restrictions of the above prior art compounds on pharmaceutical utility seem to be rather common to the indolocarbazole class of kinase inhibitors. Derivatives of the natural product K252a have also been reported to not exceed oral bioavailabilities of 10%. K252a itself showed a maximal oral bioavailability in rats of 13% and brain/plasma ratios well below 1.

These unfavorable physicochemical properties severely limit the utility of kinase inhibitors belonging to the group of glycosylated indolocarbazoles for pharmaceutical purposes, especially for the treatment of neurodegenerative and/or dementing illnesses where high brain/plasma ratios are required.

Accordingly, a need remains in the art for compounds belonging to the group of glycosylated indolocarbazoles that possess a high degree of kinase specificity and better solubility, oral bioavailability and blood-brain barrier penetration, allow a convenient synthetic access of the relevant pure enantiomers, and provide potent and efficacious inhibition of authentic PHF-tau hyperphosphorylation and inhibition of neurofibrillary degeneration.

SUMMARY OF THE INVENTION

The present invention provides compounds belonging to the group of glycosylated indolocarbazoles that possess a high degree of kinase specificity, better physicochemical properties, a convenient synthetic access of the relevant pure enantiomers, and provide potent and efficacious inhibition of authentic PHF-tau hyperphosphorylation and inhibition of neurofibrillary degeneration, and the prevention and treatment of any form of dementia that is associated with a tau pathology. The present invention is based on the realization that compounds of general formula 1 qualify for potent and efficacious inhibition of authentic PHF-tau hyperphosphorylation and inhibition of neurofibrillary degeneration, a specific utility previously not recognized for these compounds. Accordingly, compounds of general formula 1 can be used for the prevention and treatment of any one of the following diseases: Alzheimer's disease, Pick's disease, sporadic frontotemporal dementia and frontotemporal dementia with Parkinsonism linked to chromosome 17, Progressive Supranuclear Palsy (PSP), Corticobasal Degeneration (CBD) and Subacute Sclerosing Panencephalitis, (Familial) Multiple System tauopathy Dementia, Familial Gerstmann-Straussler-Scheinker Disease, Prion Protein Cerebral Amyloid Angiopathy, and other prion protein-associated diseases.

In particular, the present invention refers to the use of a indolocarbazole compound of general formula 1 or a pharmaceutically-acceptable salt thereof.

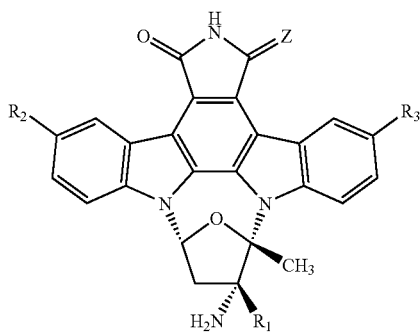

1 wherein:
R$_1$ is either COOR(R=H, methyl, ethyl or cyclopropyl) or CONHR$_4$ (R$_4$=H, methyl, ethyl or cyclopropyl), preferably CONHR$_4$, wherein R$_4$ is even more preferably H or methyl;

R$_2$ and R$_3$ are independently H, F, methyl, OH, NH$_2$ or NR$_5$R$_6$ (R$_5$ and R$_6$ independently H or methyl), preferably H; and Z is either (H, H) or O, preferably (H, H);

for the preparation of a pharmaceutical composition for the prevention or treatment of a neurodegenerative and/or dementing illness driven by the molecular pathology of microtubule-associated tau.

In a preferred embodiment the compounds of general formula 1 are employed in the form of their pharmaceutically-acceptable salts. Any pharmaceutically-acceptable salt can be employed. Preferred salts are hydrochloride, sulfate, mesylate, and p-toluol sulfonic acid salts.

Another embodiment is a method for treating or preventing a neurodegenerative and/or dementing illness driven by the molecular pathology of microtubule-associate tau, wherein the method comprises administering an effective amount of a compound of general formula 1 or a pharmaceutically-acceptable salt thereof

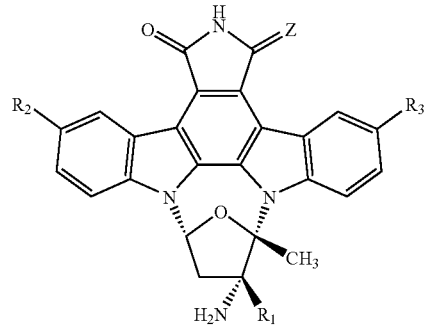

1 wherein:
R$_1$ is either COOR(R=H, methyl, ethyl or cyclopropyl) or CONHR$_4$ (R$_4$=H, methyl, ethyl or cyclopropyl);
R$_2$ and R$_3$ are independently H, F, methyl, OH, NH$_2$ or NR$_5$R$_6$ (R$_5$ and R$_6$ independently H or methyl); and
Z is either (H, H) or O;
to a subject in need thereof.

In a further embodiment, a method for the identification of inhibitors of neurofibrillary degeneration and their efficacy is described, which comprises:
(i) incubation of metabolically active brain slice tissue from a mammalian brain with candidate compounds in varying concentrations;
(ii) provocation of tau hyperphosphorylation with a PP2A inhibitor;
(iii) quantitation of tau phosphoepitopes in tissue or extracts of tissue by an immunochemical method; and
(iv) comparison of phosphoepitope provocation in said brain slice tissue exposed to varying concentrations of inhibitor compound vs. untreated control tissue.

In the present invention okadaic acid and calyculin, in particular okadaic acid, can be mentioned as examples of the PP2A inhibitor.

Yet another embodiment of the invention is a method for the determination of an appropriate dosage of an inhibitor of the paired helical filaments-type tau hyperphosphorylation for the treatment of a condition characterized by neurofibrillary pathology, wherein the method comprises:
(i) inhibitor titration in brain slices stimulated by a PP2A inhibitor to determine effective tissue concentrations; and
(ii) pharmacokinetic assessment of the dosing regimen to reach effective concentrations in the central nervous system of the subject.

Also disclosed is a method for the determination of an appropriate dosage of an inhibitor of the paired helical filaments-type tau hyperphosphorylation for the treatment of a condition characterized by neurofibrillary pathology, wherein the method comprises:
(i) determination of the normal level of a paired helical filaments-type tau phosphoepitope in cerebrospinal fluid of healthy age-matched control subjects;
(ii) increasing the dosing of an inhibitor in a single subject suffering from a form of neurofibrillar degeneration in intervals of several weeks, or exposing separate subjects to increasing doses of an inhibitor;
(iii) immunochemical assessment of the reduction of the paired helical filaments-type tau phosphoepitope in cerebrospinal fluid of the same subject immediately prior to the start of treatment and again several weeks after continued dosing with the inhibitor; and (iv) comparing the levels of paired helical filaments-type tau phosphoepitope in cerebrospinal fluid before and after the onset of treatment in an individual subject suffering from a form of neurofibrillar degeneration, and identifying the dose where the level of the paired helical filaments-type tau phosphoepitope has been reduced to the range found in healthy age-matched controls as the effective dose.

The compounds of general formula 1 solve serious problems related to unfavorable physicochemical properties associated with inhibitors of tau hyperphosphorylation disclosed in WO 00/01699 which have limited their utility for pharmaceutical purposes. The structural class of indolocarbazoles in general has been notorious for solubility, formulation and bioavailability issues. In contrast, the compounds of general formula 1 possess better solubility, oral bioavailability and blood-brain barrier penetration than previously reported for corresponding derivatives of K252a, the latter property being of particular importance for the treatment of tauopathies in the central nervous system.

Equally important are the pharmacoeconomic improvements and additional safety provided by the disclosed compounds compared to those described in WO 00/01699, which allows a convenient synthetic access of the relevant pure enantiomers.

Of the compounds of general formula 1, preferred are compounds of formula 2 and 3 in the absolute configuration corresponding to natural (+)-K252a for their combination of properties useful in the treatment of diseases characterized by neurofibrillary degeneration as well as their convenient accessibility.

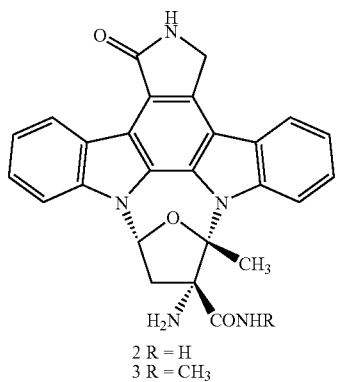

2 R = H
3 R = CH$_3$

Compounds of formula 2 and 3 can be used for the prevention and treatment of tauopathies including, but not limited to: Alzheimer's disease, Pick's disease, sporadic frontotemporal dementia and frontotemporal dementia with Parkinsonism linked to chromosome 17, Progressive Supranuclear Palsy (PSP), Corticobasal Degeneration (CBD) and Subacute Sclerosing Panencephalitis, (Familial) Multiple System tauopathy Dementia, Familial Gerstmann-Straussler-Scheinker Disease, Prion Protein Cerebral Amyloid Angiopathy, and other prion protein-associated diseases.

DETAILED DESCRIPTION OF THE INVENTION

It is to be appreciated that certain aspects, modes, embodiments, variations and features of the invention are described below in various levels of detail in order to provide a substantial understanding of the present invention. In general, such disclosure provides new methods and compositions that may be useful, alone or in combination, in the treatment of subjects in need thereof. Accordingly, the various aspects of the present invention relate to the use of specific indolocarbazole compounds for the preparation of pharmaceutical compositions for the treatment of any neurodegenerative and/or dementing illness driven by the molecular pathology of the microtubule-associated tau (hereinafter referred to as "tauopathy"). The various aspects of the present invention further relate to methods for the determination of an appropriate dosage of an inhibitor of the paired helical filaments-type tau hyperphosphorylation in vitro for the treatment of a condition characterized by neurofibrillary pathology. In other aspects, the invention provides methods for the identification of efficacious inhibitors of neurofibrillary degeneration of the invention. Accordingly, various particular embodiments that illustrate these aspects follow.

DEFINITIONS

The definitions of certain terms as used in this specification are provided below. Definitions of other terms may be found in the glossary provided by the U.S. Department of Energy, Office of Science, Human Genome Project (http://www.ornl.gov/sci/techresources/Human_Genome/glossary/).

As used herein, the term "antibody" includes, but is not limited to, polyclonal antibodies (pAbs), monoclonal antibodies (mAbs), humanized or chimeric antibodies and biologically functional antibody fragments sufficient for binding of the antibody fragment to the protein.

As used herein, the term "clinical response" means any or all of the following: a quantitative measure of the response, no response, and adverse response (i.e., side effects).

As used herein, the term "clinical trial" means any research study designed to collect clinical data on responses to a particular treatment, and includes but is not limited to phase I, phase II and phase III clinical trials. Standard methods are used to define the patient population and to enroll subjects.

As used herein, the term "effective amount" of a compound is a quantity sufficient to achieve a desired pharmacodynamic, toxicologic, therapeutic and/or prophylactic effect, for example, an amount which results in the prevention of or a decrease in the symptoms associated with a disease that is being treated, e.g., any neurodegenerative and/or dementing illness driven by the molecular pathology of the microtubule-associated tau (hereinafter referred to as "tauopathy"). The amount of compound administered to the subject will depend on the type and severity of the disease and on the characteristics of the individual, such as general health, age, sex, body weight and tolerance to drugs. It will also depend on the degree, severity and type of disease. The skilled artisan will be able to determine appropriate dosages depending on these and other factors. Typically, an effective amount of the compounds of the present invention, sufficient for achieving a therapeutic or prophylactic effect, range from about 0.001 mg per kilogram body weight per day to about 100 mg per kilogram body weight per day. Preferably, the dosage ranges are from about 1 mg per kilogram body weight per day to about 10 mg per kilogram body weight per day. The compounds of the present invention can also be administered in combination with each other, or with one or more additional therapeutic compounds.

As used herein, the term "subject" means that preferably the subject is a mammal, such as a human, but can also be an animal, e.g., domestic animals (e.g., dogs, cats and the like), farm animals (e.g., cows, sheep, pigs, horses and the like) and laboratory animals (e.g., monkey (e.g., cynmologous monkey), rats, mice, guinea pigs and the like).

As used herein, the term "tauopathy" is any form of dementia that is associated with a tau pathology. Alzheimer's disease and certain forms of frontotemporal dementia (Pick's disease, sporadic frontotemporal dementia and frontotemporal dementia with Parkinsonism linked to chromosome 17) are the most common forms of tauopathy. Other tauopathies include, but are not limited to, Progressive Supranuclear Palsy (PSP), Corticobasal Degeneration (CBD) and Subacute Sclerosing Panencephalitis, (Familial) Multiple System tauopathy Dementia, Familial Gerstmann-Straussler-Scheinker Disease, Prion Protein Cerebral Amyloid Angiopathy, and other prion protein-associated disease.

As used herein, the administration of an agent or drug to a subject or patient includes self-administration and the administration by another. It is also to be appreciated that the various modes of treatment or prevention of medical conditions as described are intended to mean "substantial", which includes total but also less than total treatment or prevention, and wherein some biologically or medically relevant result is achieved.

The details of one or more embodiments of the invention are set forth in the accompanying description below. Although any methods and materials similar or equivalent to those described herein can be used in the practice or testing of the present invention, the preferred methods and materials are now described. Other features, objects, and advantages of the invention will be apparent from the description and the claims. In the specification and the appended claims, the singular forms include plural referents unless the context clearly dictates otherwise. Unless defined otherwise, all technical and scientific terms used herein have the same meaning as commonly understood by one of ordinary skill in the art to which this invention belongs. All references cited herein are incorporated herein by reference in their entireties and for all purposes to the same extent as if each individual publication, patent, or patent application was specifically and individually incorporated by reference in its entirety for all purposes.

Kinase inhibitors belonging to the group of glycosylated indolocarbazoles have received prominent attention in the last decade for inhibiting various kinases. The most prominent members of this class are the natural alkaloide products staurosporine and K252a. These and several other derivatives were investigated mostly for therapeutic uses in various cancer indications. In a few cases, central nervous system (CNS) indications have also been contemplated, like the specific K252a derivative CEP-1347 for Parkinson's disease (PD) because of its inhibitory activity of the JNK pathway via the MLK (multi-lineage kinase) targets [Maroney et al., *J. Biol. Chem.*, 276, 25302-8 (2001)]. Unrelated to their kinase inhibitory activity, certain derivatives of K252a were also considered useful in neurodegenerative diseases due to their apparent neurotrophin agonist activity [e.g., WO 95/07911]. WO 97/05140 describes a broad range of modified K252a derivatives, with a few compounds exemplified for therapeutic use in immunosuppression and proliferative diseases (cancer) by virtue of their PKC inhibitory activity.

So far, only one disclosure has been made about specific small molecule kinase inhibitors capable of inhibiting tau hyperphosphorylation in a cell model. Certain derivatives of synthetic analogues of K252a, which in contrast to most of the other compounds in the structural class described in the prior art, are not accessible through the natural product, showed useful potency and efficacy to prevent PHF-tau hyperphosphorylation [WO 00/01699]. These compounds, however, did not show a high degree of kinase specificity, but seemed to inhibit more than one kinase, and the synthesis could only provide for racemic compounds.

The present invention is based on the realization that kinase inhibitor compounds belonging to the group of glycosylated indolocarbazoles of general formula 1 provide potent and efficacious inhibition of authentic PHF-tau hyperphosphorylation and inhibition of neurofibrillary degeneration, a specific utility previously not recognized for these compounds.

The compounds of the present invention provide additional important advantages over the compounds in the prior art. The structural class of indolocarbazoles in general has been notorious for solubility, formulation and bioavailability issues. In contrast, the compounds of general formula 1 possess better solubility, oral bioavailability and blood-brain barrier penetration than previously reported for corresponding derivatives of K252a, the latter property being of particular importance for the treatment of tauopathies in the central nervous system. Accordingly, the compounds of the present invention solve serious problems related to unfavorable physicochemical properties associated with inhibitors of tau hyperphosphorylation disclosed in WO 00/01699, which have limited their utility for pharmaceutical purposes.

Other equally important advantages of the present invention include the pharmacoeconomic improvements and additional safety provided by the compounds of the present invention. In contrast to the prior art compounds that did not show a high degree of kinase specificity, seemed to inhibit more than one kinase, and the synthesis could only provide for racemic compounds [see WO 00/01699], the compounds of the present invention provide higher kinase specificity and allow a convenient synthetic access of the relevant pure enantiomers.

Preparation of the Compounds

The compounds of general formula 1 can be prepared from commercially available staurosporine, e.g., by using the methods described in WO 97/05140 and generally established functional group chemistry disclosed in the context of indolocarbazole derivatization in the prior art [e.g., WO 94/02488]. These documents are incorporated herein by reference. Multi-gram amounts of the preferred compound of formula 3 are prepared by reacting the respective carboxymethyl derivative of the compound of general formula 1 ($R_1$=COOCH$_3$, obtained as in WO 97/05140, with methylamine in tetrahydrofuran. Alternatively, the carboxymethyl derivative may first be hydrolyzed under alkaline conditions according to WO 97/05140 and then reacted with methylamine in tetrahydrofuran in the presence of a condensing reagent, e.g., 1,1'-dicarbonyldiimidazole. To improve the solubility in vehicles for oral application in any in vivo experiment the compound of formula 3 can be converted into salt form, e.g., its hydrochloride salt, by adding the necessary amounts of the corresponding acid to a solution of the compound of formula 3 in tetrahydrofuran, followed by evaporation of the solvent.

A Method for the Identification of Inhibitors of Neurofibrillary Degeneration and their Potency/Efficacy:

The present invention provides a method for the identification of inhibitors of neurofibrillary degeneration and their efficacy. The method comprises the following steps:

(i) incubation of metabolically active brain slice tissue from a mammalian brain with candidate compounds in varying concentrations;

(ii) provocation of tau hyperphosphorylation with a PP2A inhibitor;

(iii) quantitation of tau phosphoepitopes in tissue or extracts of tissue by an immunochemical method; and (iv) comparison of phosphoepitope provocation in said brain slice tissue exposed to varying concentrations of inhibitor compound vs. untreated control tissue.

In step (i), metabolically active brain slices can be obtained by resection of brain tissue, preferably hippocampi, from freshly sacrificed adult rats and preparation of slices with a tissue chopper. After recovery, for example, in a physiological low calcium buffer the slices can then be preincubated in the same buffer but in the presence of physiological calcium concentrations with the candidate compound, preferably a compound of the general formula 1, at varying concentrations ranging, e.g., from 30 nM to 10 µM at 34 to 37° C. for e.g., 15 min. Thereafter, step (ii) is carried out by adding a PP2A inhibitor, for example, for at least 1 h. Preferably okadaic acid at 1 µM is used. For step (iii), the slices can be extracted (e.g., by sonication) with a non-denaturing buffer containing reagents to stop kinases, phosphatases, and proteases. Prior to immunochemical analysis, the extracts may be subjected to brief boiling to enrich tau proteins, which remain soluble under these conditions, in the extract. Using conventional immuno-blotting techniques (e.g., Western-blotting) or alternatively ELISA techniques using a phosphorylation-dependent tau antibody, it is possible to measure the amount of a PHF-type tau phosphoepitope in a sample of extract containing a fixed amount of protein by development e.g., with commercial staining or chemoluminescence kits, followed by densitometry (immuno-blots), or direct measurement of absorbance or emission of light (ELISA). For greater accuracy, the signals obtained in this fashion may be normalized to the amount of total tau, which is determined by the same techniques but using a phosphorylation-independent tau antibody. The normalized quantity of the tau phosphoepitope of interest is then given by the ratio of tau phosphoepitope over total tau in arbitrary units of intensity. Finally, step (iv) comprises the comparison of the optionally normalized amount of pathological tau phosphoepitope in the presence of varying concentrations of tau hyperphosphorylation inhibitor with the maximum amount induced by the PP2A inhibitor alone. The concentration of tau hyperphosphorylation inhibitor reducing the provocation of a PHF-tau phosphoepitope by 50% is deemed to be partially effective. On the other hand, the minimal concentration of tau hyperphosphorylation inhibitor reducing the amount of PHF-tau phosphoepitopes to normal levels found in brain slices in the absence of any provocation by a PP2A inhibitor is the lowest completely effective concentration.

Methods for the Determination of an Appropriate Dosage of an Inhibitor of the Paired Helical Filaments-Type Tau Hyperphosphorylation for the Treatment of a Condition Characterized by Neurofibrillary Pathology Two methods for determining an appropriate dosage of an inhibitor of the paired helical filaments-type tau hyperphosphorylation for the treatment of a condition characterized by neurofibrillary pathology are also described. In both cases, the subject can be any mammal. In one embodiment, the mammal is a human. In an alternative embodiment, the mammal is an experimental animal, which is optionally sacrificed after the method has been conducted.

In the first method the following steps are conducted:
(i) inhibitor titration in a brain slices stimulated by a PP2A inhibitor according to the previous method, to determine effective tissue concentrations; and
(ii) pharmacokinetic assessment of the dosing regimen to reach effective concentrations in the central nervous system of the subject.

A preferred embodiment of this step is discussed in the following: Hereby the tau hyperphosphorylation inhibitor, preferably a compound of general formula 1, is administered to a subject by any appropriate route of delivery, preferably orally, in various doses. The concentration of the compound over time can be assessed by measuring the amount of compound in fixed volumes of plasma taken repeatedly over a period of time after dosing. To this end, the compound can be exhaustively extracted by a non-water miscible organic solvent and quantified in arbitrary units, e.g., by HPLC, preferably with photometric or fluorometric detection methods. The absolute amount of the compound is then obtained by comparison of these values to a standard curve established by extraction of plasma samples previously spiked with a known amount of the compound ex vivo. The time of maximal plasma concentration is chosen to then measure in a separate test series the amount of compound in the brain. For animal subjects, the brains are resected after the appropriate post-administration interval, then exhaustively extracted with a non-water miscible organic solvent, e.g., by use of sonication, and the amount of compound is then established by HPLC in a fashion identical to the procedure with plasma. In human subjects, the amount of the compound can be measured non-invasively by quantitative Magnetic Resonance Imaging (MRI). For sufficient sensitivity of this method, the compound can be administered in an isotopically-labelled form suitable for this purpose, e.g., by incorporation of $^{13}C$ isotope at synthetically convenient positions of the inhibitor molecule.

The second method is particularly suitable for human subjects and comprises the following steps:
(i) determination of the normal level of a paired helical filaments-type tau phosphoepitope in cerebrospinal fluid of healthy age-matched control subjects;
(ii) increasing the dosing of an inhibitor in a single subject suffering from a form of neurofibrillar degeneration in intervals of several weeks, or exposing separate subjects to increasing doses of an inhibitor;
(iii) immunochemical assessment of the reduction of the paired helical filaments-type tau phosphoepitope in cerebrospinal fluid of the same subject immediately prior to the start of treatment and again several weeks after continued dosing with the inhibitor; and
(iv) comparing the levels of paired helical filaments-type tau phosphoepitope in cerebrospinal fluid before and after the onset of treatment in an individual subject suffering from a form of neurofibrillar degeneration, and identifying the dose where the level of the paired helical filaments-type tau phosphoepitope has been reduced to the range found in healthy age-matched controls as the effective dose.

A preferred embodiment of this method is now discussed.

In step (i), a reference range of control values for a PHF-tau phosphoepitope, preferably those relating to phosphorylations of $Thr_{231}$ or $Ser_{422}$, is determined in healthy subjects. The subjects are suitably of the age where the respective neurodegenerative disease tends to have its time of onset. For example, 2 to 15 ml of cerebrospinal fluid are drawn by lumbar puncture. Equal aliquots of such samples are then analyzed, e.g., in generally available ELISA kits. For greater accuracy, the samples subjected to analysis may be normalized to comparable total protein content. For greater sensitivity of the test, the samples may be concentrated prior to use by vacuum evaporation. The highest level of tau phosphoepitope of any verified healthy subject may then be taken as the "acceptable level," provided the subject does not show signs of a neurodegenerative disease within one year after sampling.

Step (ii) consists of administration of an inhibitor of tau hyperphosphorylation, preferably a compound of general formula 1, to subjects clinically diagnosed with a disease characterized by neurofibrillary pathology by virtue of established functional criteria. The diagnosis may be supported by biomarker criteria, most conveniently those relating to tau phosphoepitopes in cerebrospinal fluid as established in the context of a pre-administration test under step (iii). The dose of the compound can either stepped up in intervals of several weeks in any given patient, or a different doses can be administered to each subject in a study cohort. In addition, separate dosing intervals can be employed.

In step (iii), cerebrospinal fluid from each patient subject to treatment with a tau hyper-phosphorylation inhibitor, preferably a compound of general formula 1, is sampled immediately prior to administration of compound 1 to establish a pathological reference level of a PHF-tau phosphoepitope by use of the same analytical means and procedures as used under step (i). Treatment is initiated thereafter with the inhibitor, whereby a dosing regimen according to step (ii) is employed. From each patient another cerebrospinal fluid sample is drawn after several weeks of continuous treatment with any dose of inhibitor, and analyzed in direct reference to the respective pre-treatment samples of each subject. To this end, duplicate pre-treatment cerebrospinal fluid samples as well as healthy control samples (step (i)) are tested again simultaneously on the same ELISA plate as the post-treatment samples, confirming at the same time the stability and reproducibility of the test.

Finally, in step (iv), the dose and/or chronic application regimen of inhibitor, either determined by dose-escalation within an individual subject, or by separate fixed dosing regimen within subject groups, which suppresses the levels of a PHF-tau phosphoepitope below the "acceptable level" (see step (i)) is deemed a fully effective chronic dose. Any level higher than that, but lower than the pre-treatment level in an individual subject, is a partially effective dose for that individual subject.

Determination of Active Concentrations for Inhibition of PHF-Type Tau Hyperphosphorylation in a Central Nervous System Tissue Model The concentration which the compounds of general formula 1 need to have in situ in order to effectively inhibit PHF-type tau hyperphosphorylation is evaluated in a tissue model of freshly prepared metabolically active adult rat hippocampal brain slices, a model previously not known to be useful for this purpose. Authentic PHF-type phosphorylation events virtually indistinguishable by all known molecular markers from what is seen in PHF-tau from human Alzheimer's disease brains is rapidly provoked in such brain slices by application of the phosphatase inhibitor okadaic acid (OA) [Gong et al., Brain Res. Brain Res. Protoc., 6, 134-140 (2001); WO 01/57535; WO 00/01699].

There are a multitude of criteria for PHF-type tau hyperphosphorylation, most of them comprising reactivity with monoclonal antibody recognizing specific sites of phosphorylation among the total of more than 20 phosphorylation sites of tau, all of which are maximally phosphorylated in the PHF-state of tau. The majority of those sites belong to the class of so-called "proline-directed" sites, invariably characterized by a Ser-Pro or Thr-Pro motif. The phosphorylation of these motifs has profound effects on the conformation of the protein. Site-directed phosphorylation-sensitive antibodies reporting phosphorylations, e.g., at $Ser_{199}$, $Ser_{202}$, $Thr_{205}$, $Thr_{231}$, $Ser_{235}$, $Ser_{396}$, $Ser_{404}$ and $Ser_{422}$, are now routinely available from a variety of sources. A few phosphoepitopes are especially specific for PHF-tau as they are completely absent in normally phosphorylated tau. Examples are the epitope of the mAb AT100 with a complex epitope dependent on both phosphorylation and conformation, and most notably mAb AP422, solely dependent on $Ser_{422}$ phosphorylation of tau. The particular simplicity of the latter antibody's epitope restrictions make it a particularly useful diagnostic criteria for all authentic PHF-type tau phosphorylation events in vitro as well as in vivo [WO 01/57535]. Besides the above phosphorylation motif, a few non-proline-directed phosphorylation sites have also been linked specifically to the PHF-tau phosphorylation state, like $Ser_{262}$, which is located within the domain of tau responsible for its binding to microtubule.

Another highly characteristic criterion for the PHF-tau-like phosphorylation state is the maximally retarded electrophoretic mobility on SDS-PAGE gels, reporting the combined conformation-altering effects of the full array of proline-directed phosphorylation. In this state, PHF-tau has lost its ability to bind to microtubule, an functional deficit which can be fully reversed by dephosphorylation.

In okadaic acid-treated brain slices, most of the above pathological markers are modeled. For the detection of active inhibitor compounds, freshly prepared metabolically-active isolated slices, kept under constant oxygenation in a physiological buffer (artificial cerebrospinal fluid or Krebs-Ringer solution), are preincubated with a range of concentration of the compounds of general formula 1. The slices are then extracted with buffers stopping both kinase as well as phosphatase activities, and soluble supernatants of such tissue homogenates are then separated by SDS-PAGE and subjected to Western-blotting. Immunoblots are developed by standard methods with mono- or polyclonal antibodies directed against site-specific phosphorylation motifs of tau, including but not limited to $Thr_{181}$, $Ser_{199}$/$Ser_{202}$/$Thr_{205}$ (mAb AT8), $Thr_{212}$, $Thr_{231}$ (mAb AT100), $Ser_{235}$, $Ser_{262}$, $Ser_{396}$ (mAb PHF-1), $Ser_{404}$ and $Ser_{422}$ (mAb AP422). The intensity of the signals can then be normalized to the amount of total tau in the sample by probing a sister blot with a phosphorylation insensitive tau antibody, followed by forming the intensity ratio of the respective phosphoepitope over total tau immunoreactivity which represent an accurate quantitative measure of the degree of phosphorylation defining a particular epitope. It is easily appreciated by anyone skilled in the art that similar analysis may be carried at greater speeds with ELISA techniques using the same type of immunochemical reagents. Alternatively, the analysis can also be performed by use of generally established staining antibody techniques in situ on thin sections of frozen tissue or paraffin-embedded tissue previously fixed with formaldehyde, glutaraldehyde, or similar modified fixatives.

Remarkably, compounds of general formula 1, and especially compounds of formula 2 and 3, prevent the provocation of the entire complement of all these PHF-markers by okadaic acid in spite of the very general nature of phosphorylation effects induced by phosphatase inhibition. The compounds are essentially able to arrest and preserve the normal physiological pattern of tau phosphorylation in brain slices, which is similar to the phosphorylation pattern in vivo. The potency of the compounds ranges from $IC_{50}$ values of 200 nM (like in the case of the compounds of formula 2 and 3) to >10 μM. Detailed analysis of dose-response behavior reveals that, equally surprising, all PHF-tau markers are co-titrated by the active compounds at rather similar $IC_{50}$ values, suggesting that PHF-tau hyperphosphorylation is not as heterogeneous an event as it may be expected based on the nature of the stimulating agent okadaic acid. Tau hyperphosphorylation is generally completely suppressed at concentrations of $10 \times IC_{50}$. At such fully efficacious concentrations, however, the underlying normal phosphorylation pattern is not yet affected, suggesting a certain selectivity of the compounds in vivo for pathological vs. physiological tau phosphorylation events. From these data, it can be deduced that for, e.g., for the compounds of formula 2 or 3, a brain concentration of at least 1 µM is desirable for complete suppression of PHF-type tau hyperphosphorylation.

The efficacy of the compounds of general formula 1 specifically for tauopathy-related phosphorylation is not a frequently observed feature of the indolocarbazole compound class. Certain indolocarbazole kinase inhibitors of the prior art, like CEP-1347 (a substituted K252a-derivative), or the parent compound staurosporine are inactive in the brain slice hyperphosphorylation model, although these kinase inhibitors, especially the latter, are not very specific and inhibit a multitude of kinases potently. In view of this, the efficacy of specific compounds of general formula 1 could not be anticipated.

Determination of Dosing to Reach Efficacious Concentrations of Compounds of General Formula 1 In Vivo in the Central Nervous System The potential of a limited set compounds related to the compounds of general formula 1 as inhibitors of tau hyperphosphorylation has been recognized before in WO 00/01699. However, the physicochemical properties of this series of compounds are very poor, resulting in the need to use non-GRAS vehicles for compound application. In addition, even under specialized conditions of application, oral bioavailability for the prior art compounds usually does not exceed 10% in rats [WO 95/22331]. Possibly related to these unfortunate properties, half-lives in rats after i.v. application are unattractively short at about 1 h. Brain/plasma ratios determined in vivo as the concentration of the compound in brain over the concentration of the compound in plasma at a given time point are also poor, and deteriorate further when GRAS-vehicles are used, suggesting an unacceptable influence of vehicle on these parameters. Chronic in vivo experiments for the inhibition of neurofibrillary pathology in authentic models, like transgenic mice carrying human pathogenic mutations of tau, cannot be conducted with such compounds.

Unfortunately, the restrictions of the above prior art compounds on pharmaceutical utility seem to be rather common to the indolocarbazole class of kinase inhibitors. Derivatives of the natural product K252a have also been reported to not exceed oral bioavailabilities of 10%. K252a itself showed a maximal oral bioavailability in rats of 13% and brain/plasma ratios well below 1.

In view of these known difficulties and since chronic efficacy studies in animal models or human subjects are very time consuming and expensive, it is desirable to assess central nervous system exposure to compounds of general formula 1 relative to dosing by suitably designed pharmacokinetic studies. The effective concentration, as determined by the tissue model above, defines the target exposure in vivo. Surprisingly, representative compounds of the general formula 1, especially when applied in salt form, improved oral bioavailability in rats 2-3 fold over the examples cited above, and brain/plasma ratios approached or even exceeded one, possibly suggesting an active uptake mechanism across the blood-brain barrier. This finding is of particular relevance for the central nervous system application of these kinase inhibitors, since their kinase selectivity is not very high. Thus, even moderate improvements in brain penetration allow for lower exposure of peripheral tissues and therefore reduce the risk of non-central nervous system side effects due to moderate kinase selectivity. Another important advantage is that satisfactory application could generally be performed solely with GRAS-vehicles. Presumably related to better physicochemical properties, half-lives also improved to a more satisfactory range, up to a few hours in the case of the compound of formula 3 after i.v. application in rats. It is appreciated by anyone skilled in the art that similar studies are applicable to other species, e.g., mice. In the case of human subjects, non-invasive imaging techniques to assess compound penetration into the central nervous system, e.g., after isotopic labeling of a compound of general formula 1 suitable for MRI studies.

This behavior together with the fortuitous tau hyperphosphorylation inhibitor activity proves that compounds of general formula 1, and particularly of formula 2 and 3, are useful for the treatment of the chronic central nervous system conditions represented by Alzheimer's disease and the group of tauopathies in general at a clinically feasible dosing range (e.g., 5-20 mg/kg).

Treatment of Neurodegenerative Conditions Characterized by Authentic Neurofibrillary Pathology in Experimental Animal Models Generally, neurofibrillary pathology is never observed at any relevant level in any wild-type species other than humans. This has greatly hampered the investigation of this type of neurodegeneration up to a point that even the relevance of this phenomenon as part of a primary disease mechanism was put in doubt. With the discovery that certain tauopathies with the full spectrum of biochemical abnormalities and neuronal dysfunction can emanate from a variety of single tau mutations, the causal role of tau in such disease processes was proven. Moreover, the introduction of human pathogenic mutations of tau in transgenic mice allowed the modeling of authentic pathology in small experimental animals, opening the road for conclusive proof of concept tests of therapeutic agents. However, the role of pathological tau phosphorylations associated with the formation of paired helical filaments in the causality of the disease process remained ambiguous, i.e., it was not obvious whether abnormal tau phosphorylation is upstream or downstream the causative chain producing neurotoxic tau aggregation, or whether it is merely an epiphenomenon of the tau pathology. Efficacy of inhibitors of tau hyperphosphorylation for neurofibrillary degenerative conditions could only reasonably be expected if tau hyperphosphorylation was both upstream and causative for aggregation.

As an example for a familial tauopathy, the mutation P301L in tau (a mutation in the "hinge" region of one of the microtubule-binding repeat domains) causes a familial form of FTDP (frontotemporal dementia with Parkinson) in humans around the age of 50-60 years [Hutton at al., Nature 393, 702-705 (1998)]. In mice, transgenic with such a mutated form of human tau, when expression is driven by a prion promoter to protein levels similar to endogenous mouse tau, mice succumb to a motor disease phenotype similar to ALS (amyotrophic lateral sclerosis) with onset of disease between 8-12 months of age [Lewis et al., Nature Genet., 25, 402-405 (2000)]. The phenotype is distinct from the human counterpart (mainly frontal pathology) because in these mice distribution of neurofibrillary pathology is mainly in the spinal cord and parts of the hind brain/brain stem, affecting primarily the motor system. This difference is actually an advantage, because the read-out of deficits of motor function can be conducted in a much more robust fashion than other more subtle deficits like memory or psychiatric phenotypes are accessible in mice. Thus, it is possible to use very objective tests to define onset of pathology for such mice. For the motor deficits, e.g., a combination of "wire hang test" and "beam balance test" or other similar tests known in the art which are sensitive to hind limb performance, is conveniently used in regular intervals to monitor the performance of the transgenic mice from about 8 months on. Stringent onset criteria are constructed from repeated failure of a combination of such tests in such a way as to exclude the identification of false positives, i.e., mice which temporarily recover again after meeting criteria. Therefore, proof of concept data with mice of such phenotype as the P301L-transgenic mice is very reliable and predictive for the clinical utility in the human pathology.

The P301L-tau transgenic mice deteriorate very rapidly 2-3 weeks after onset into a moribund state due to an extraordinarily aggressive progression of the pathology, orders of magnitude faster than what is observed in human patients with or without tau mutations where the tauopathy usually progresses over several years as is also the case in Alzheimer's disease. Therefore, transgenic mouse models of this type must be considered very "hard" models wherein effective drugs might be easily missed. Conversely, if efficacy is in fact observed in such a challenging model, it must be considered as a highly significant result. Other less aggressive transgenic mouse models using wild-type human tau have been developed recently, e.g., by knock-out/knock-in strategies, wherein the endogeneous mouse gene is replaced by a genomic human tau construct allowing for expression of the full human complement of 6 tau splice isoforms [Andorfer et al., *J. Neurochem.*, 86, 582-90 (2003)]. Such mice show onset at later age, slower progression and milder, more complex phenotypes. They may be useful for testing less efficacious therapeutic strategies at the expense of a much longer testing schedule and the need for more sophisticated read-outs. However, apart from the issues of utility, the demonstration that authentic tau pathology can also be produced in animals without pathogenic mutations is insofar significant as the vast majority of tauopathies as well as Alzheimer's disease are not caused by mutations. Evidently tauopathies, like Alzheimer's disease, are of multifactorial origin but always end in a common malignant pathway of tau pathology.

The compounds disclosed herein are sufficiently efficacious to be tested in the aggressive P301L-tau transgenic mouse model. Immediately prior to the expected onset window, i.e., from about 8 months on in the case of P301L-tau transgenic mice, a compound like the compound of formula 3, preferably in salt form, is administered twice daily to a suitable mutant tau transgenic mouse by oral gavage at doses ranging from 10 mg/kg to 20 mg/kg in the case of compound of formula 3. It is appreciated by anyone skilled in the art that dosing may be adjusted for any individual compound according to the results of titration in the brain slice model and pharmacokinetic studies described above. The compound can be given as a solid in a variety of solid dosage formulations known in the art, or dissolved in a minimal amount of liquid like PEG400 for optimal dispersion. During the treatment, motor performance of treated and untreated P301L-tau transgenic mice are continuously assessed by a simple wire hang test in combination with a beam balance test. Mean times of onset are recorded between treated and control group, and significance is calculated using the respective variances, e.g., by a standard ANOVA statistical test. Mice are sacrificed when (i) they have reached a moribund state, or (ii) at the end of the experimental treatment window, usually no longer than 3 months. Additional confirmation of the efficacy of the treatment is then obtained post-mortem by using standard biochemical and histological assessment of PHF-tau hyperphosphorylation and the formation of neurofibrillary tangles. For the analysis of biochemical PHF-phosphorylation markers, aliquots of fresh tissue from spinal cord or other affected parts of the central nervous system are extracted in detergent-free buffers and the amount of pathologically phosphorylated tau in low-speed supernatants is determined by Western-blotting with diagnostic mAbs like AP422 or other tau phosphoepitope dependent antibodies known in the art, similar to the analysis performed with brain slices (see above). This analysis is aided in P301L-tau transgenic mice by the fact that the hyperphosphorylated human tau protein has a uniquely retarded gel mobility on standard SDS-PAGE relative to the normally phosphorylated mixture of transgenic human and endogenous mouse tau proteins. Subjecting the low-speed supernatants to a 100,000×g centrifugation leads to sedimentation of almost the entire amount of the hyperphosphorylated tau species of abnormal gel mobility. Therefore, although suspendable during extraction, the hyperphosphorylated tau proteins formed in P301L-tau transgenic mice are essentially of insoluble nature.

To determine the impact of inhibition of tau hyperphosphorylation on the aggregation of tau protein, the amount of hyperphosphorylated human tau protein in the low speed supernatants of the spinal cord or brain extracts can be assessed with a phosphorylation-independent human specific mAb like HT7, and its quantitated signal may be normalized for variations of transgene expression levels by forming a ratio over the total amount of human transgenic tau (both normally and abnormally phosphorylated) in the respective samples. The compound of the formula 3 reduced the various tau phosphoepitope signals as well as the total human tau signal to a similar extent, demonstrating that inhibition of hyperphosphorylation resulted in a corresponding reduction of the formation of insoluble PHF-tau in low-speed supernatants. It is thus clear that hyperphosphorylation of tau is an integral step in the causal event cascade leading to PHF pathology.

Other aliquots of the affected CNS tissues are sectioned for standard histological assessment of aggregated tau in form of neurofibrillary tangles or neuropil threads by suitable silver-staining methods (e.g., Gallyas staining) or immunohistochemistry with phosphoepitope sensitive mAbs (e.g., AT8). Generally, however, there is not a correlation between the reduction of hyperphosphorylated tau species by the compound of the formula 3 in low speed extract supernatants and histologically-detectable tangle counts, suggesting that former pool of insoluble tau species, but not the mature tangles are the main neurotoxic species.

By all of the above functional and pathological criteria compounds of general formula 1, but especially the compound of formula 3, are effective to postpone the onset of pathology and disease phenotype, in the case of the compound of formula 3 by at least 6 weeks, and to significantly slow the progression of the disease significantly in this aggressive model.

In summary, it is surprising that an in vitro brain slice tissue model using a completely artificial method of biochemical provocation (e.g., by okadaic acid) has been found in this invention to be so accurately predictive for efficacy in a pathological model characterized by tau protein aggregation with an as yet obscure pathogenesis and with very different time scales involved (hours vs. weeks/months). Thus, this aspect of the invention should greatly facilitate the identification and relevant dosing of therapeutic agents useful in treating central nervous system diseases characterized by neurofibrillary degeneration.

Treatment of Human Patients Suffering from Alzheimer's Disease or Other Forms of Tauopathies Classical Alzheimer's disease is defined by the coexistence of two types of pathological protein deposits in the brains of affected subjects. Mainly extracellular deposition of Aβ, a short aggregating peptide derived from the membrane protein APP, is one of the major hallmarks. The other is per definitionem intracellular aggregation of abnormally hyperphosphorylated tau into PHF (tauopathy). No neurodegeneration was observed in several transgenic mouse lines with sole deposition of Aβ. On the other hand, several mutant tau transgenic mouse lines showing neurofibrillary tangles all had massive neurodegenerative phenotypes without exception. This mirrors the human situation, where brains of non-demented older patients often show extensive Aβ pathology without other abnormalities, like neurofibrillary tangles, Lewy bodies or vascular abnormalities. In contrast, the occurrence of a high density of neurofibrillary tangles in any brain region, even if not accompanied by any other pathological features ("pure tauopathy"), is invariably correlated with serious functional deficits, depending on the brain regions affected.

Present evidence in the art argues stringently that the tauopathy is the primary malignant pathological feature, even in indications where other pathological markers coexist. The treatment with inhibitors of tau hyperphosphorylation is thus indicated in all those diseases, most notably Alzheimer's disease. While the clinical diagnosis of many of the more prominent pure tauopathies, like frontotemporal degeneration, corticobasal degeneration or Pick's disease, is often quite clear cut because of their unique symptomatology [Kertesz A., *Neurologist*, 9, 311-317 (2003)], the unequivocal diagnosis of classical Alzheimer's disease is more challenging because a smaller fraction of clinically diagnosed patients often suffers from a significant contribution of cerebrovascular arteriosclerosis or Lewy inclusion body pathology, together with Aβ pathology, producing a similar symptomatology like classical Alzheimer's disease dominated by neurodegeneration driven by neurofibrillary tangles.

To verify that a patient diagnosed clinically with Alzheimer's disease by standard psychometric assessment batteries or imaging techniques prevalent in the current practice is indeed subject to treatment with compounds of general formula 1, additional specific biomarker tests relating to the involvement of tau in the disease are performed. Cerebrospinal fluid from suspected patients is obtained by lumbar spinal taps and levels of tau proteins are measured by generally available ELISA tests. Elevated levels confirm the diagnosis for Alzheimer's disease [Andreasen et al., *Neurology*, 53, 1488-94 (1999)]. Further diagnostic accuracy is obtained by measuring specific phosphoepitopes, e.g., those relating to phosphorylation of $Thr_{231}$, which indicate a prominent contribution of tau phosphorylation pathology in the respective Alzheimer's disease patients [e.g., Hampel et al., *Arch. Gen. Psychiatry*, 61, 95-102 (2004)].

A subject diagnosed by one or a sum of the above criteria with Alzheimer's disease or any other tauopathy is treated, for example, with a once or twice daily dose of 100 to 1000 mg of a compound of general formula 1 which can be applied orally or rectally. The precise dosing in each individual patient will depend on various factors such as the age and weight of the patient as well as the severity of the disease and is determined advantageously by using the same cerebrospinal fluid tau phosphoepitope ELISA tests used for diagnosis (see above). Prior to initiation of treatment, a cerebrospinal fluid sample of several milliliters is taken by lumbar puncture to measure the base level of pathological tau phosphorylation markers for the subject. The subject is then subjected to an escalating dose schedule. After four weeks of treatment with any given dose, another cerebrospinal fluid sample is taken for repeated determination of tau phosphoepitope levels. The minimal dose sufficient for this subject is the one where tau phosphoepitope levels return to the average level in age-matched healthy controls. This test can also be used for single doses in a merely confirmatory manner. Suitable antibodies for such tests recognize phosphorylation of tau on sites including but not limited to $Thr_{181}$, $Ser_{199}$, $Ser_{202}$, $Thr_{205}$, $Ser_{235}$ and $Ser_{396}$, but especially $Thr_{231}$ or $Ser_{422}$, or a combination of such specific phosphorylation sites like $Thr_{231}/Ser_{235}$ etc. The duration of the treatment is for as long as the condition persists, usually for the remainder of a subject's life. The compounds can be administered as pharmaceutically-acceptable salts formed with inorganic or organic acids, including but not limited to chloride, sulfate, phosphate, mesylate, p-toluol sulfonate, formiate, acetate, benzoate, salicylate, malate, tartrate, citrate, lactate, etc.

Pharmaceutical compositions for oral application may contain inactive ingredients such as sugars, e.g., lactose or sorbitol, cellulose preparations, e.g., methyl cellulose, various forms of starch, gelatin, cyclodextrins, polyvinylpyrrolidone, talc, stearic acid and salts thereof, polyethylene glycol in various degrees of polymerization, e.g., PEG400. Alternatively, dry filled capsules made from gelatin, with or without commonly used plasticizers, may be used. For rectal administration compositions may also contain inactive ingredients as a suppository base. These include but are not limited to triglycerides, paraffins, PEG or higher alcohols.

Formulations and Methods of Treatment

Compositions intended for oral use may be prepared according to any method known to the art for the manufacture of pharmaceutical compositions and such compositions may contain one or more compounds selected from the group consisting of sweetening compounds, flavoring compounds, coloring compounds and preserving compounds in order to provide pharmaceutically elegant and palatable preparations. Tablets contain the active compound in a mixture with non-toxic pharmaceutically-acceptable excipients that are suitable for the manufacture of tablets. These excipients may be for example, inert diluents, such as calcium carbonate, sodium carbonate, lactose, calcium phosphate or sodium phosphate; granulating and disintegrating compounds, for example, corn starch, or alginic acid; binding compounds, for example starch, gelatin or acacia, and lubricating compounds, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Aqueous suspensions contain the active material in admixture with excipients suitable for the manufacture of aqueous suspensions. Such excipients are suspending compounds, for example sodium carboxymethylcellulose, methylcellulose, hydropropylmethylcellulose, sodium alginate, polyvinylpyrrolidone, gum tragacanth and gum acacia; dispersing or wetting compounds may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring compounds, one or more flavoring compounds, and one or more sweetening compounds, such as sucrose or saccharin.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening compound, for example beeswax, hard paraffin or acetyl alcohol. Sweetening compounds such as those set forth above, and flavoring compounds may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting compound, suspending compound and one or more preservatives. Suitable dispersing or wetting compounds and suspending compounds are exemplified by those already mentioned above. Additional excipients, for example sweetening, flavoring and coloring compounds, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying compounds may be naturally occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example sweetening, flavoring and coloring compounds, may also be present.

Syrups and elixirs may be formulated with sweetening compounds, for example glycerol, propylene glycol, sorbitol or sucrose. Such formulations may also contain a demulcent, a preservative and flavoring and coloring compounds. The pharmaceutical compositions may be in the form of a sterile injectable aqueous or oleaginous suspension. This suspension may be formulated according to the known art using those suitable dispersing or wetting compounds and suspending compounds which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or diglycerides. In addition, fatty acids such as oleic acid find use in the preparation of injectables.

The active compound may also be administered in the form of suppositories for rectal administration of the drug. These compositions can be prepared by mixing the drug with a suitable non-irritating excipient, which is solid at ordinary temperatures but liquid at the rectal temperature and will therefore melt in the rectum to release the drug. Such materials are cocoa butter and polyethylene glycols.

The active compound may be administered parenterally in a sterile medium. The drug, depending on the vehicle and concentration used can either be suspended or dissolved in the vehicle. Advantageously, adjuvants such as local anesthetics, preservatives and buffering compounds can be dissolved in the vehicle.

Compositions of the present invention (i.e., kinase inhibitors belonging to the group of glycosylated indolocarbazoles as defined above in Formulas 1, 2, and 3) may be administered continuously or intermittently by any route which is compatible with the particular molecules. Thus, as appropriate, administration may be oral or parenteral, including subcutaneous, intravenous, inhalation, nasal, and intraperitoneal routes of administration. In addition, intermittent administration may be by periodic injections of a bolus of the composition once daily, once every two days, once every three days, once weekly, twice weekly, biweekly, twice monthly, and monthly.

Therapeutic compositions of the present invention may be provided to an individual by any suitable means, directly (e.g., locally, as by injection, implantation or topical administration to a tissue locus) or systemically (e.g., parenterally or orally). Where the composition is to be provided parenterally, such as by intravenous, subcutaneous, intramolecular, ophthalmic, intraperitoneal, intramuscular, buccal, rectal, vaginal, intraorbital, intradermal, transdermal, intratracheal, intracerebral, intracranial, intraspinal, intraventricular, intrathecal, intracisternal, intracapsular, intranasal or by aerosol administration, the composition preferably comprises part of an aqueous or physiologically compatible fluid suspension or solution. Thus, the carrier or vehicle is physiologically acceptable so that in addition to delivery of the desired composition to the patient, it does not otherwise adversely affect the patient's electrolyte and/or volume balance. The fluid medium for the agent thus can comprise normal physiologic saline (e.g., 0.9% aqueous NaCl) or a buffer, pH 3-7.4. Alternatively, the use of continuous or pulsatile administration of the therapeutic compositions of the present invention by mini-pump can be employed in the methods of the present invention.

Useful solutions for parenteral administration may be prepared by any of the methods well known in the pharmaceutical art, described, for example, in Remington's Pharmaceutical Science (Gennaro, A., ed.), Mack Pub., 1990. Formulations of the therapeutic agents of the invention may include, for example, polyalkylene glycols such as polyethylene glycol, oils of vegetable origin, hydrogenated naphthalenes, and the like. Formulations for direct administration, in particular, may include glycerol and other compositions of high viscosity to help maintain the agent at the desired locus. Biocompatible, preferably bioresorbable, polymers, including, for example, hyaluronic acid, collagen, tricalcium phosphate, polybutyrate, lactide, and glycolide polymers and lactide/glycolide copolymers, may be useful excipients to control the release of the agent in vivo. Other potentially useful parenteral delivery systems for these agents include ethylene-vinyl acetate copolymer particles, osmotic pumps, implantable infusion systems, and liposomes. Formulations for inhalation administration contain as excipients, for example, lactose, or may be aqueous solutions containing, for example, polyoxyethylene-9-lauryl ether, glycocholate and deoxycholate, or oily solutions for administration in the form of nasal drops, or as a gel to be applied intranasally. Formulations for parenteral administration may also include glycocholate for buccal administration, methoxysalicylate for rectal administration, or cutric acid for vaginal administration. Suppositories for rectal administration may also be prepared by mixing the therapeutic compositions of the present invention (alone or in combination with a chemotherapeutic agent) with a non-irritating excipient such as cocoa butter or other compositions that are solid at room temperature and liquid at body temperatures.

Where the kinase inhibitor compound of the present invention is given by injection, it can be formulated by dissolving, suspending or emulsifying it in an aqueous or nonaqueous solvent. Methyl sulfoxide, N,N-dimethylacetamide, N,N-dimethylformamide, vegetable or similar oils, synthetic aliphatic acid glycerides, esters of higher aliphatic acids and proylene glycol are examples of nonaqueous solvents. The compound is preferably formulated in aqueous solutions such as Hank's solution, Ringer's solution or physiological saline buffer.

Where the kinase inhibitor compound is given orally, it can be formulated through combination with pharmaceutically-acceptable carriers that are well known in the art. The carriers enable the compound to be formulated, for example, as a tablet, pill, suspension, liquid or gel for oral ingestion by the patient. Oral use formulations can be obtained in a variety of ways, including mixing the compound with a solid excipient, optionally grinding the resulting mixture, adding suitable auxiliaries and processing the granule mixture. The following list includes examples of excipients that can be used in an oral formulation: sugars such as lactose, sucrose, mannitol or sorbitol; cellulose preparations such as maize starch, wheat starch, potato starch, gelatin, gum tragacanth, methyl cellulose, hydroxyproylmethyl-cellulose, sodium carboxymethyl-cellulose and polyvinylpyrrolidone (PVP).

The kinase inhibitor compounds of the present invention can also be delivered in an aerosol spray preparation from a pressurized pack, a nebulizer or from a dry powder inhaler. Suitable propellants that can be used in a nebulizer include, for example, dichlorodifluoro-methane, trichlorofluoromethane, dichlorotetrafluoroethane and carbon dioxide. The dosage can be determined by providing a valve to deliver a regulated amount of the compound in the case of a pressurized aerosol.

Formulations for topical administration to the skin surface may be prepared by dispersing the molecule capable of releasing the therapeutic compositions of the present invention (alone or in combination with a chemotherapeutic agent) with a dermatologically acceptable carrier such as a lotion, cream, ointment or soap. Particularly useful are carriers capable of forming a film or layer over the skin to localize application and inhibit removal. For topical, administration to internal tissue surfaces, the agent may be dispersed in a liquid tissue adhesive or other substance known to enhance adsorption to a tissue surface. For example, hydroxypropylcellulose or fibrinogen/thrombin solutions may be used to advantage. Alternatively, tissue-coating solutions, such as pectin-containing formulations may be used.

The kinase inhibitor compounds of the present invention can be used in the treatment of any neurodegenerative and/or dementing illness driven by the molecular pathology of the microtubule-associated tau (hereinafter referred to as "tauopathy"). The compounds of the present invention can be provided simultaneously or sequentially in time. The compounds of the present invention can be administered alone or in combination with other therapeutic agents, e.g., neural growth factor compounds, acetyl cholinesterase inhibitors, or compounds reducing the levels of β-amyloid peptide.

Pharmaceutical compositions of the present invention contain a therapeutically effective amount of a compound of the present invention. The amount of the compound will depend on the patient being treated. The patient's weight, severity of illness, manner of administration and judgment of the prescribing physician should be taken into account in deciding the proper amount. The determination of a therapeutically effective amount of a kinase inhibitor compound of the present invention is well within the capabilities of one with skill in the art.

Although a therapeutically-effective amount of a kinase inhibitor compound will vary according to the patient being treated, suitable doses will typically be in the range between about 0.001 mg/kg and about 10 g/kg of the compound. An alternative suitable dose range is between about 0.1 mg/kg and about 500 mg/kg of the compound. Yet another alternative suitable dose range is between about 1 mg/kg and about 100 mg/kg of the compound.

In some cases, it may be necessary to use dosages outside of the stated ranges to treat a patient. Those cases will be apparent to the prescribing physician. Where it is necessary, a physician will also know-how and when to interrupt, adjust or terminate treatment in conjunction with a response of a particular patient.

The invention is further defined by reference to the following examples, which are not meant to limit the scope of the present invention. It will be apparent to those skilled in the art that many modifications, both to the materials and to the methods, may be practiced without departing from the purpose and interest of the invention. Compounds of the present invention may be tested for efficacy in vitro and in vivo in experimental animal models using the assay described below; an effective compound will inhibit tau hyperphosphorylation and tau protein aggregation both in vitro and in experimental animal models described below. Preferred compounds of the invention are those that have the greatest effects in experimental animal models. The following examples illustrate the invention described above, but do not imply any limitation of scope beyond the disclosure above.

EXAMPLES

In the examples, the following abbreviations are employed:

| | |
|---|---|
| $CaCl_2$ | calcium chloride |
| $CO_2$ | carbon dioxide |
| DMSO | dimethylsulfoxide |
| ECL | enhanced chemoluminescence |
| EDTA | ethylene diamine tetraacetic acid |
| EGTA | ethylene glycol-bis(2-aminoethyl ether)-N,N,N',N'-tetraacetic acid |
| HEPES | N-2-hydroxyethyl-piperazine-N'-2-ethanesulfonic acid |
| $IC_{50}$ | half-maximal inhibitory concentration |
| i.v. | intravenous |
| HPLC | high performance liquid chromatography |
| h | hour |
| KCl | potassium chloride |
| kg | kilogram |
| $KH_2PO_4$ | potassium dihydrogen phosphate |
| $MgSO_4$ | magnesium sulfate |
| mAb | monoclonal antibody |
| min | minute |
| ml | milliliter |
| μM | micromolar |
| mM | millimolar |
| mm | millimeter |
| NaCl | sodium chloride |
| $NaHCO_3$ | sodium hydrogen carbonate |
| nM | nanomolar |
| OD | optical density |
| pAb | polyclonal antibody |
| PEG | polyethylene glycol |
| PHF | paired helical filaments |

| | |
|---|---|
| PMSF | p-Methylphenylsulfonylfluoride |
| P301L mutant tau | tau with proline at position 301 replaced by leucine |
| 4R0N splice isoform | tau with 4 microtubule-binding repeat domains, no N-terminal inserts |
| SDS-PAGE | sodium dodecylsulfate polyacrylamide gel electrophoresis |
| Ser | serine |
| Thr | threonine |

Example 1

Titration of Tau Hyperphosphorylation Inhibitors in a Rat Hippocampal Brain Slice Model Adult male Wistar rats of about 300 gram weight (3 months old) were briefly anesthetized with $CO_2$ and decapitated. The brains were removed within 2 min and the hippocampus was dissected using a blunt spatula. The hippocampi were cut into 0.45 mM slices using a McIlwain tissue chopper and placed into ice-cold low calcium Krebs-bicarbonate buffer (pH 7.0): 124 mM NaCl, 3.33 mM KCl, 0.01 mM $CaCl_2$, 1.25 mM $KH_2PO_4$, 1.33 mM $MgSO_4$, 25.7 mM $NaHCO_3$, 10 mM D-glucose and 20 mM HEPES. 5-8 slices were placed into a tube with 5 ml of low calcium buffer and incubated for at least 30 min at 33-34° C. with water saturated oxygenation (95% $O_2$, 5% $CO_2$). After 30 min, the solution was replaced with a buffer containing a physiological level of calcium (1.3 mM) and incubated for an additional 30 min. After a total equilibration period of at least 1 hr, the slices were preincubated for 15 min with concentrations of the compound of general formula 1 of up to 10 μM. Appropriate dilutions of the compound of general formula 1 were prepared from 10 mM stock solutions in DMSO to provide for a final DMSO concentration of 0.5% in the incubation solution. Thereafter, the slices were exposed to 1 μM okadaic acid for 1 h. After this treatment, the buffer was removed and the slices were sonicated for 10-20 seconds in 0.5 ml "homogenization buffer" (100 mM $KH_2PO_4$, pH 6.5, 2 mM EGTA, 2 mM EDTA, 0.5 mM PMSF and 2 μM okadaic acid) containing a cocktail of protease inhibitors: 100 μM PMSF, 10 μg/ml aprotinin, 10 μM leupeptin, 6 μg/ml pepstatin and 40 μM chymostatin. Homogenates were centrifuged for 30 min at 16,000×g, supernatants were collected, heated for 5 min to 100° C. and centrifuged again. Aliquots of heat-stable supernatants, normalized for protein content, were analyzed on 10% SDS-PAGE, followed by immunoblotting with mAbs AT8 (anti-$Ser_{202}$/$Thr_{205}$; 1:200), AP422 (anti-$Ser_{422}$; 1:5,000), AT100 and anti-$Ser_{262}$ and anti-$Thr_{231}$ pAbs. Blots were developed by ECL (Amersham Life Sciences) and exposed to a Kodak X-OMAT AR film. Phosphoepitope formation was quantified by densitometric analysis of properly exposed films (OD<1.5) by forming the ratio of intensities of the phosphoepitope in question over total tau immunoreactivity determined by mAb Tau-1 (1:5,000) after thorough dephosphorylation of tau proteins on the blot, accomplished by extensive incubation of sister-blots with high concentrations of calf intestinal phosphatase.

Cursory assessment of the inhibition of tau hyperphosphorylation was performed at 10 μM compound, followed by detailed titration of the compounds from 30 nM to 10 μM. $IC_{50}$ values are defined as the concentration of the compound of general formula 1, where the phosphoepitope intensity ratio as determined above was reduced by 50% relative to the positive control value obtained with okadaic acid alone in the absence of inhibitor. The compounds of formula 2 and 3 had $IC_{50}$ values in the range of 200-400 nM for AP422, AT8, AT100, anti-$Thr_{231}$, and anti-$pSer_{282}$.

Example 2

Determination of the Dosage for Required Brain Exposure In Vivo for the Compound of Formula 3

In order to assess the dosage for required in vivo brain exposure, 10 mg/kg of the hydrochloride of the compound of formula 3 in a vehicle of 1.5 ml/kg PEG 400 Macrogol Ph. Eur. were applied i.v. through the femoral vein to two groups (n=3) of overnight fasted Wistar Rats weighing between 240-270 gram. The application was performed under anesthesia, initiated with 3.5% Isofluorane/$O_2$, then maintained at 1% during compound application and suture of the vein. 200 μl of local anesthetic lidocaine were administered locally. One hour after application of the compound 200 μl of blood were obtained by tail vein incision. Immediately following the blood sampling, rats were terminated by decapitation after brief $CO_2$ anesthesia. Brains and spinal cords were resected and weighed. Plasma was obtained by centrifugation of the tail vein blood at 13000×g for 20 minutes at 4° C. Using the methods described below in more detail, a plasma half-life of about 4 hrs was determined for 3 after oral application of 5 mg/kg. The concentrations found in CNS tissue were similar to those found in plasma indicating a satisfactory penetration of the blood-brain barrier.

Extraction of the Compound of Formula 3 from Plasma

In a glass tube, 200 μl concentrated ammonia solution and 200 μl saturated NaCl solution were mixed with each plasma sample obtained from an equal volume of blood. The mixture was extracted with 2 ml ethylacetate (HPLC grade) by vigorous vortexing for 1 minute to form a fine emulsion. After accelerated phase separation by centrifugation at 4000×g for 5-10 minutes at room temperature the organic phase was collected with a glass pipette and evaporated in a glass vial in a vacuum evaporator at 50-60° C. The aqueous phase was extracted a second time in an identical fashion, and the organic phase was combined with the first extract.

Extraction of the Compound of Formula 3 from Brain

One half of a rat brain was placed in a conical bottom glass tube and homogenized in 500 μl saturated NaCl solution by sonication (Bandelin Sonoplus UW 2070, Berlin) at 55% power for 20 seconds at 4° C. 200 μl concentrated ammonia was added to the samples. Extraction was then performed with 2×2 ml ethylacetate (HPLC grade) as with the plasma samples. A similar procedure was applied to spinal cord samples.

Establishment of Extraction Recovery and Standard Curve for the Compound of Formula 3

100 μl plasma or 0.5 gram brain tissue homogenate in saturated NaCl, obtained from control rats, were spiked with the compound of formula 3, respectively, to produce concentrations ranging from 1 ng/ml to 5 μg/ml. The spiked brain or plasma samples were then subjected to the extraction and processing as described above. Quantitative analysis of the extracts was performed by HPLC with fluorescence detection. Residues after evaporation of combined organic extracts were taken up in 300 μl acetonitrile and 100 μl were injected onto a 5 μm RP 18 Select B 12.5×4.6 mm column (Merck) at a flow rate of 0.75 ml/min. Elution was isocratic at a temperature of 40° C. with acetonitrile/water 60/40 (v/v). Fluorescence detection and quantitation by peak area was performed with a G1321A (Agilent Tech 1100 series) detector at excitation and emission wavelengths of 284 nm and 476 nm. The peak areas were compared against those obtained after injection of several concentrations of pure standard derived from a stock solution of the compound of formula 3 in acetonitrile (HPLC grade) to determine extraction efficiencies, which were routinely 90-95%. The standard curve was obtained by plotting amounts of pure standard injected in µg vs. fluorescent peak area.

Example 3

Treatment of P301L-tau Transgenic Mice, Suffering from Neurofibrillary Degeneration A cohort of 61 transgenic mice of the same age, homozygous for the 4R0N splice isoform of human P301L-mutant tau transgene (JNPL3 line, obtainable from Taconic Farms, NY), is divided into two groups comprising 30 mice to receive treatment with the compound of formula 3 and 31 mice to receive vehicle only or, alternatively, to remain untreated (controls).

The therapeutic regimen in the treatment group is initiated as soon as the first mouse shows symptoms of motor deficits, usually around 8 months after birth; this mouse is thereafter excluded from the control group, reducing the group size to 30 mice. The treatment schedule comprises the application by oral gavage of twice daily a dose of 10 mg/kg of the compound of formula 3 dissolved as the hydrochloride salt in PEG400 Macrogol Ph. Eur. at a concentration of about 5 mg/ml. The compound is administered early in the morning and late in the evening to mice fasted at least 6 hours prior to drug administration. Simultaneously with initiation of drug treatment, a regular motor performance testing schedule with strict formal criteria for onset of disease is commenced as described below. Both treatment and testing are continued for at least 3 months, at which time all mice are sacrificed which have not yet become moribund after disease onset. The moribund stage is reached when the mice become unable to feed themselves.

Motor performance testing consists of daily assessment of the mice in a wire hang test and a beam balance test, each carried out in duplicate during the same testing session, but not in immediate succession for any given mouse to avoid tiring. The wire hang test simply requires mice to be able to hold on to an inverted cage grid for at least 60 seconds after they were allowed to grasp the grid with their forelimbs only. For the beam balance test mice must cross a narrow elevated beam between two platforms. To detect early impending signs of hind limb problems, the time taken for crossing as well as the number of hind limb slippings is recorded.

To provide for a balance between stringency of criteria on the one hand, and sensitivity on the other hand for time of onset uncontaminated by false positives, i.e., mice where performance rebounds after seemingly having failed criteria, it is required that sick mice either fail at least one of the tests in duplicate for two consecutive days, or fail both tests at least once in the duplicate testing for two consecutive days.

Times of onset for the treatment group vs. the control group are graphed in a survival curve. Mean times of onset with standard deviations are compared to calculate the statistical significance of treatment effect between the groups by a one-way ANOVA, Fisher's post-hoc test. Animals which die from unrelated causes, i.e., without the typical symptoms of the tauopathy, are excluded from consideration. According to these criteria, only two mice achieved the full criteria of severe disease in a cohort of about 30 animals treated with twice daily oral applications of 10 mg/kg kinase inhibitor 3 for a period of three months (commencing with the observation of initial symptoms in the first mouse of the control cohort), while in the equally sized vehicle treated control cohort, more than half of the animals reached the same criteria of full-blown motor symptoms ($P<0.005$).

After sacrificing, central nervous system tissue from each mouse is resected for biochemical analysis of tau phosphorylation effects and histological assessment of tau pathology by standard neuropathological techniques. One half of each hind brain and spinal cord is subjected to extraction in "homogenization buffer" and quantitation of PHF-like phosphorylated tau by Western-blot analysis of the homogenate supernatants with phosphoepitope antibodies. The other half of the tissue is subjected to fixation in 4% formaldehyde and then subjected to sectioning. Serial sections of hind brain and spinal cord tissue are stained for neurofibrillary tangles by the Gallyas silver staining technique [Munoz, *Biotech. Histochem.*, 74, 311-320 (1999)] and by phosphoepitope mAbs commonly used in human neuropathology, like PHF-1 and AT8. Neurofibrillary tangles are counted in multiple sections of the same tissue within defined microscopic fields. In addition, the more diffuse staining in neuropil due to neuropil threads (also consisting of paired helical filaments) is scored semi-quantitatively as O, +, ++, +++by a blinded investigator. Neurofibrillary tangle counts as well as neuropil thread scores are then statistically compared between the treated and the control group by ANOVA analysis and Fisher's post-hoc test.

The Western-blot analysis of insoluble hyperphosphorylated tau species in mouse brain extracts is carried out as follows: Samples of brain or spinal cord tissues of treated or untreated mice are homogenized by sonication immediately after resection in a 10-20 fold amount of ice-cold extraction buffer composed of 100 mM $KH_2PO_4$, pH 6.5, 2 mM EGTA, 2 mM EDTA, 0.5 mM PMSF, 1 µM OA, and 10 µg/ml leupeptin. After centrifugation at 13,000×g for 5 min at 4° C., the supernatants are collected and their total protein content is determined. Aliquots of the supernatants, normalized for equal load of total extract protein, are loaded on a 8% Tris-glycine SDS-PAGE and blotted onto nitrocellulose membranes after electrophoretic separation by standard Western-blotting techniques. The blots are blocked with a 3% solution of dry milk or any other suitable inert protein and subsequently exposed to a number of antibodies in suitable dilution (e.g., AP422 1:4,000, AT8 1:1,000, anti-$pSer_{262}$ 1:5,000) and developed after labeling with a secondary antibody (e.g., HRP-linked goat-anti-mouse pAb for monoclonal primary Abs, and HRP-linked goat-anti-rabbit pAb for polyclonal primary Abs, at dilutions of about 1:5,000) using the Amersham ECL-kit. The signals on the ECL-film are quantitated using digital densitometry (ImageQuant, Biorad). While PHF-specific mAbs like AP422 and AT8 recognize only the pathologically phosphorylated transgenic tau with its characteristically retarded gel mobility (64 kD in the P301L-tau mouse model), other antibodies like anti-$pSer_{262}$ also label the normally phosphorylated tau proteins with an apparent molecular weight around 55 kD, consisting of a mixture of unaffected transgenic human tau and endogenous mouse tau, which generally does not participate in the molecular pathology. Only the quantitation of the abnormal tau proteins in the 64 kD band is employed for the determination of the efficacy of the kinase inhibitor 3. Since all 64 kD species are removed from the supernatant fraction after centrifugation at 100,000× g, it is clear that the entire population of abnormally phosphorylated tau species in the original 13,000×g extract supernatant are of insoluble nature. With the human tau specific mAb HT7, a normalized measure of global pathological activity can be obtained by forming the ratio of the 64 kD signal over the sum of the 55 kD and 64 kD signals, which is most favorably used as a central criterion for the efficacy of kinase inhibitor 3 in preventing neurofibrillary pathology.

According to this criterion, a cohort treated twice daily with 10-200 mg/kg kinase inhibitor 3 p.o. in a vehicle consisting of a minimal amount of PEG400 (for solubilization of the compound at 37° C.) forms, on average, over 50% less insoluble pathologically modified 64 kD tau than the vehicle treated control cohort, since all 64 kD tau signals, i.e., the phosphorylation-independent tau signal of HT7 as well as the phosphoepitopes of AP422, AT8 and anti-pSer$_{262}$ (only 64 kD population) are reduced by about the same amount (P=0.015-0.004).

EQUIVALENTS

The present invention is not to be limited in terms of the particular embodiments described in this application, which are intended as single illustrations of individual aspects of the invention. Many modifications and variations of this invention can be made without departing from its spirit and scope, as will be apparent to those skilled in the art. Functionally equivalent methods and apparatuses within the scope of the invention, in addition to those enumerated herein, will be apparent to those skilled in the art from the foregoing descriptions. Such modifications and variations are intended to fall within the scope of the appended claims. The present invention is to be limited only by the terms of the appended claims, along with the full scope of equivalents to which such claims are entitled.

I claim:

1. A method for inhibiting hyperphosphorylation of tau, wherein the method comprises administering an effective amount of a compound of general formula 3 or a pharmaceutically-acceptable salt thereof

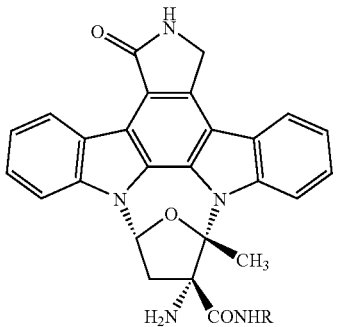

wherein R=CH$_3$,
to a subject in need thereof.

2. The method according to claim 1, wherein such inhibitory effect will treat a disease selected from the group consisting of: Alzheimer's disease, frontal lobe dementia, Pick's disease, Parkinson disease with dementia, corticobasal degeneration, argyrophilic grains disease, progressive supranuclear palsy, subacute sclerosing panencephalitis, multiple system tauopathy dementia, and familial Gerstmann-Straussler-Scheinker Disease.

3. An indolocarbazole compound of formula 3 or a pharmaceutically-acceptable salt thereof,

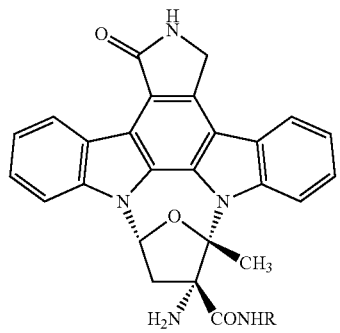

wherein R=CH$_3$.

4. The method according to claim 1, wherein such inhibitory effect will treat Alzheimer's disease.

* * * * *